United States Patent
Lian et al.

(10) Patent No.: US 8,419,645 B2
(45) Date of Patent: Apr. 16, 2013

(54) RESPIRATION MEASUREMENT BY MEANS OF MORPHOLOGICAL OPERATORS

(75) Inventors: Jie Lian, Beaverton, OR (US); Dirk Muessig, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 18 days.

(21) Appl. No.: 13/176,484

(22) Filed: Jul. 5, 2011

(65) Prior Publication Data

US 2011/0263987 A1  Oct. 27, 2011

Related U.S. Application Data

(63) Continuation-in-part of application No. 12/252,529, filed on Oct. 16, 2008, now Pat. No. 8,315,694.

(51) Int. Cl.
*A61B 5/08* (2006.01)
(52) U.S. Cl.
USPC .................................................. 600/484
(58) Field of Classification Search .......... 607/20; 600/484
See application file for complete search history.

(56) References Cited

U.S. PATENT DOCUMENTS

| 5,817,133 | A  | * | 10/1998 | Houben ............................ 607/9 |
| 5,891,048 | A  |   | 4/1999  | Nigam |
| 6,076,015 | A  | * | 6/2000  | Hartley et al. .................. 607/20 |
| 6,470,215 | B1 |   | 10/2002 | Kraus et al. |
| 6,574,509 | B1 |   | 6/2003  | Kraus |
| 6,622,043 | B1 |   | 9/2003  | Kraus |
| 7,187,965 | B2 |   | 3/2007  | Bischoff |
| 7,228,173 | B2 |   | 6/2007  | Cazares |
| 2003/0023178 | A1 | | 1/2003 | Bischoff et al. |
| 2004/0158295 | A1 | | 8/2004 | Dyjach |
| 2005/0234361 | A1 | | 10/2005 | Holland |
| 2006/0111751 | A1 | | 5/2006 | Cazares |
| 2007/0265667 | A1 | | 11/2007 | Muessig |

OTHER PUBLICATIONS

European Search report dated Dec. 21, 2011, 5 pages.

* cited by examiner

*Primary Examiner* — Christopher D Koharski
*Assistant Examiner* — Philip Edwards
(74) *Attorney, Agent, or Firm* — ARC IP Law, PC; Joseph J. Mayo

(57) ABSTRACT

An implantable medical device that measures respiration parameters based on transthoracic impedance signals, and converts transthoracic impedance signals into a time series of digital values which is filtered with morphological operators to separate the signal into a respiratory component and a cardiac component. Metrics are generated based on the filtered impedance values such as respiratory rate, I/E ratio, tidal volume and minute ventilation.

18 Claims, 16 Drawing Sheets

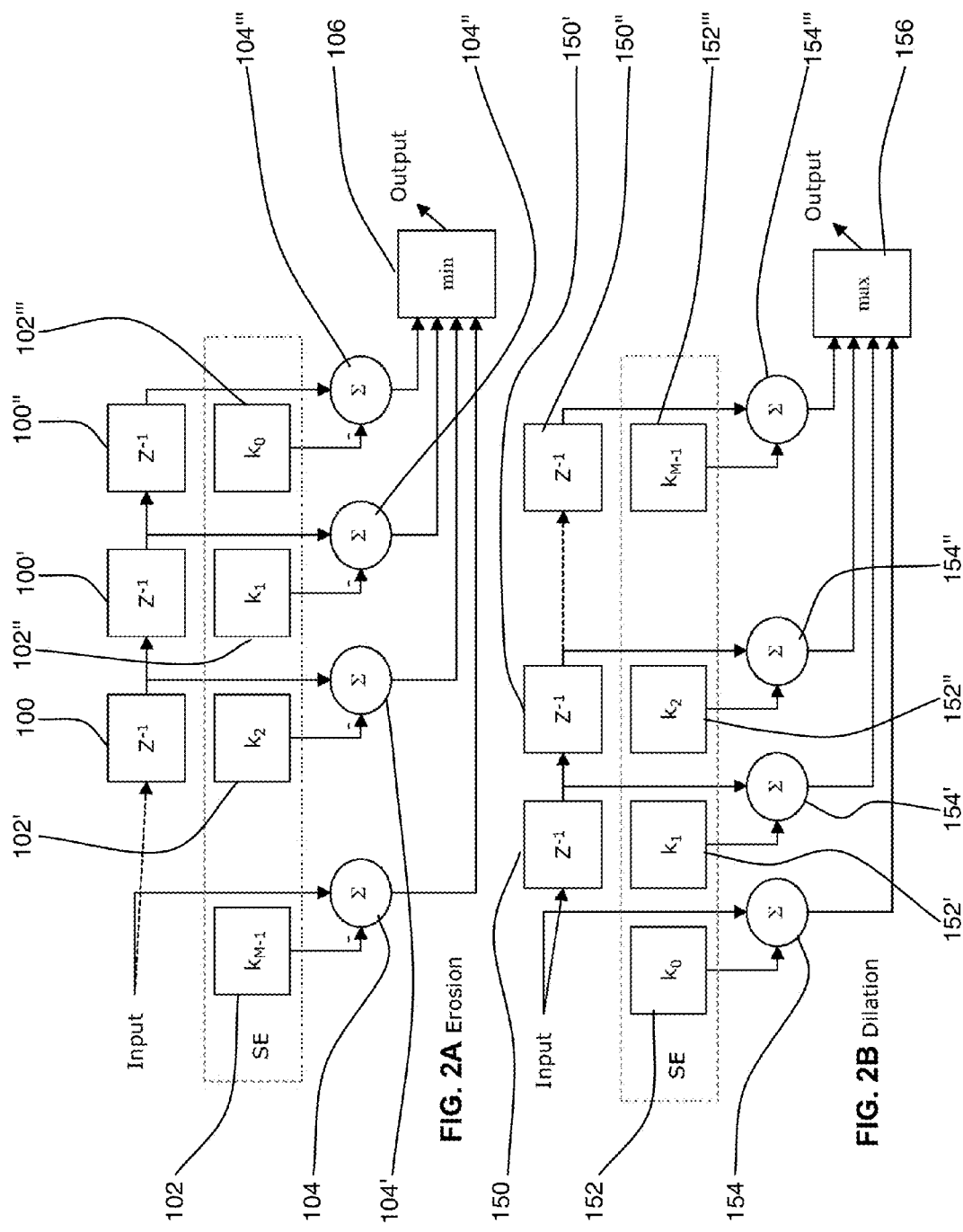

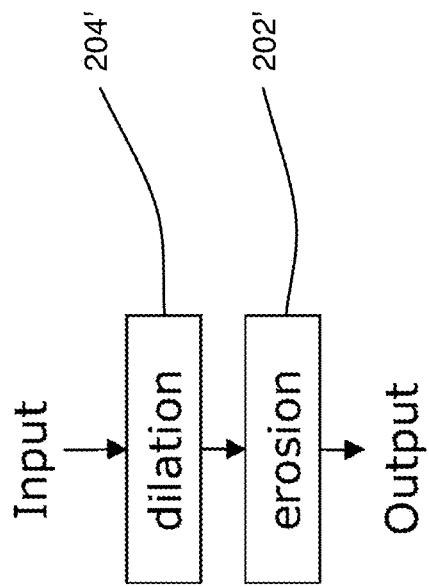
FIG. 3B Closing
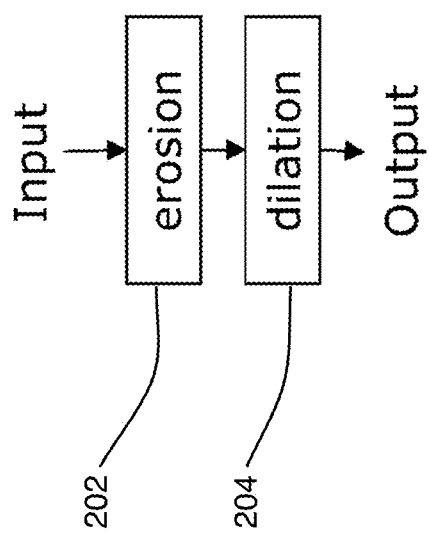
FIG. 3A Opening

FIG. 4B
FIG. 4A
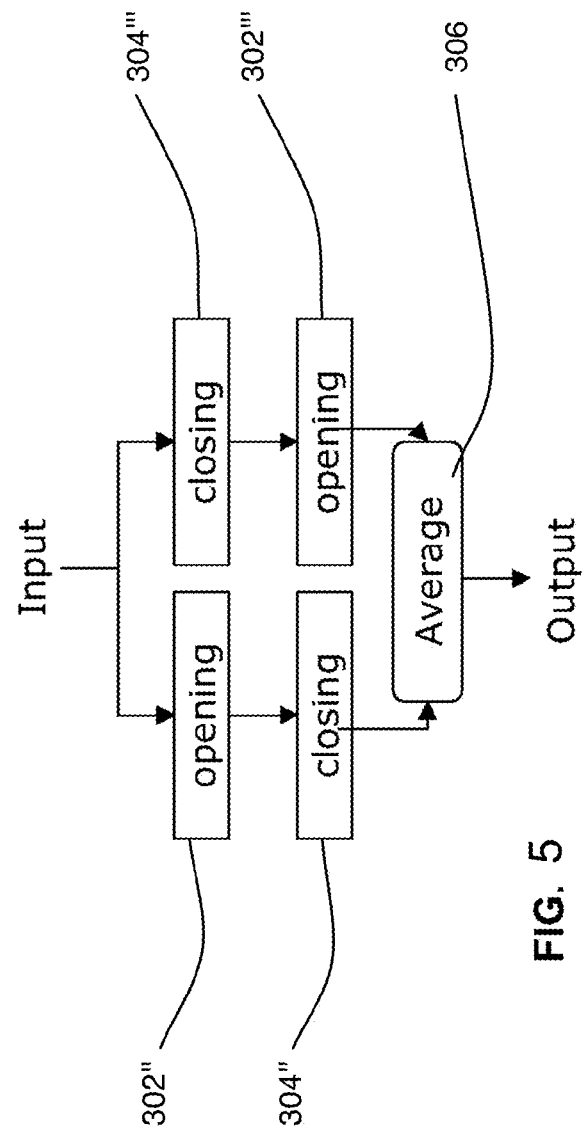
FIG. 5

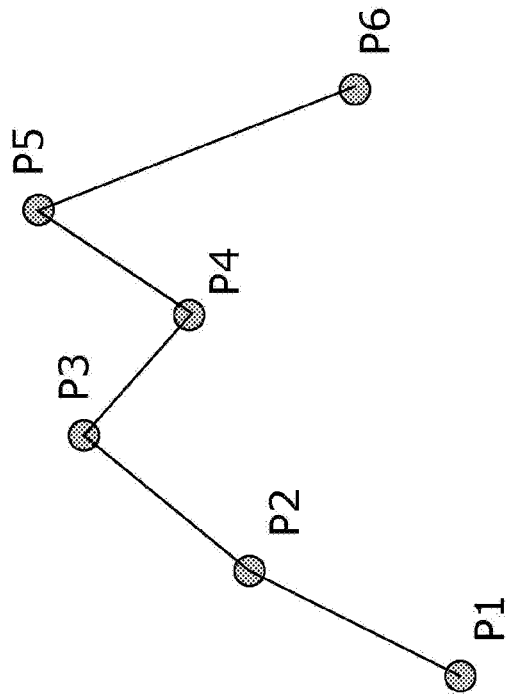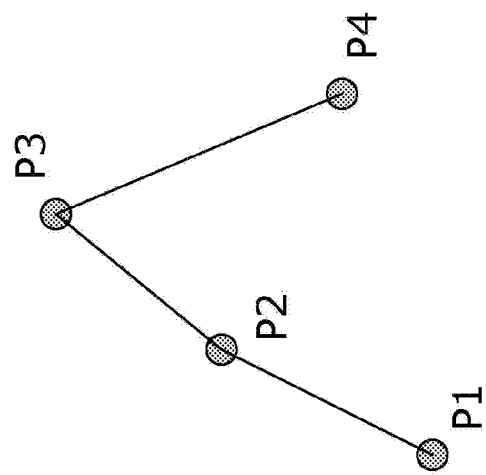
Figure 13

RESPIRATION MEASUREMENT BY MEANS OF MORPHOLOGICAL OPERATORS

This application is a continuation in part of U.S. Utility patent application Ser. No. 12/252,529, filed 16 Oct. 2008, now U.S. Pat. No. 8,315,694 the specification of which is hereby incorporated herein by reference.

BACKGROUND OF THE INVENTION

1. Field of the Invention

Embodiments of the invention generally relate to medical devices that measure respiration parameters based on transthoracic impedance signals. More particularly, but not by way of limitation, one or more embodiments of the invention enable a method and apparatus that converts transthoracic impedance signals into a time series of digital values which is filtered with morphological operators to divide the signal into a respiratory component and a cardiac component and further extract metrics such as respiratory rate, inspiration/expiration (I/E ratio), tidal volume and minute ventilation.

2. Description of the Related Art

There are no known methods or apparatus that can both robustly and efficiently extract respiration information from the transthoracic impedance signal. All known devices that attempt to extract respiration information from impedance signals rely on specially designed finite-impulse response (FIR) filters to remove the cardiac component of the impedance signal while attempting to retain the respiration component of the signal. Although the respiration signal and cardiac signal have different dominant frequencies, the frequency spectrums of these signals do overlap. Therefore, the morphology of the respiration signal extracted from the impedance signal after applying these filters is often distorted. External noises in the impedance signal, such as baseline wander and impulse artifacts, can negatively affect the filter performance. In addition, the complex filters described require special hardware or firmware design, which adds complexity to the implantable device and their operation require more computation power.

Morphological operators have been widely used in 2D image processing for noise removal, and have shown to have better edge preservation performance than other linear or nonlinear filters. The morphological operators have very high computation efficiency, and can be implemented in hardware platform, thus they are particularly suitable for application in low-power devices. However, the application of morphological operators in 1D signal processing, in particular biomedical signal processing has been limited. Morphological operators were used to implement a peak-valley extractor for QRS complex detection in ECG signals. Another morphological approach was developed to detect QRS complexes and remove baseline wander in neonatal ECG signals. Such approach was disclosed in U.S. Pat. No. 5,817,133 issued to Houben, for discriminating P waves from far-field R waves in an implantable pacemaker. However, there are no known solutions that utilize morphological operators to determine respiration parameters from a transthoracic impedance signal.

BRIEF SUMMARY OF THE INVENTION

It is an object of one or more embodiments of the invention to provide a novel apparatus and method to extract respiration parameters from a transthoracic impedance signal recorded by an implantable medical device. Example respiration parameters or metrics that embodiments of the invention are configured to obtain include but not limited to respiration rate, tidal volume, inspiration/expiration (I/E ratio), and minute ventilation for example.

One or more embodiments of the invention are configured to apply non-linear morphological filters to the transthoracic impedance signal measured by the implantable device to remove the cardiac component while retaining the respiratory component of the signal. The filtered respiratory component of the impedance signal is then subjected to further processing to extract the metrics such as respiratory rate, I/E ratio, tidal volume, and minute ventilation for example.

Embodiments of the invention utilize the novel concept that when viewing the lower-frequency respiratory component (Zr) of the impedance signal, the higher-frequency cardiac component (Zc) can be treated as embedded "impulse noise". Even though the duration of a Zc cycle can be as wide as 1 second, it can still be viewed as an "impulse" compared to the slowly changing Zr signal. Therefore, morphological operators can be applied to the transthoracic impedance signal to effectively remove the Zc impulses while preserving the Zr component In one or more embodiments, the morphological signal analyzer or microprocessor programmed as such is configured to generate modified time series of the impedance values by applying both, an erosion operator and a dilation operator to the time series to thus obtain a modified time series of values representing a trend of values of the first time series. The erosion operator and the dilation operator both are morphological operators.

In one or more embodiments, the method of generating a modified time series includes applying both, an erosion operator and a dilation operator to the first time series to thus obtain the modified time series of values representing a trend of values of said first time series. The erosion operator and a dilation operator are both morphological operators. The method of generating a modified time series may further include applying an erosion operator followed by a dilation operator that together form an opening operator to suppress peaks in the first time series. Likewise, the method of generating a modified time series may further include applying a dilation operator followed by an erosion operator that together form a closing operator to suppress pits in the first time series.

The details of embodiments of the invention can be understood from the following drawings and the corresponding text descriptions.

BRIEF DESCRIPTION OF THE DRAWINGS

The above and other aspects, features and advantages of embodiments of the invention will be more apparent from the following more particular description thereof, presented in conjunction with the following drawings wherein:

FIG. 2A shows the circuit block diagram for implementing the erosion operator, and FIG. 2B shows the circuit block diagram for implementing of the dilation operator.

FIG. 3A shows the block diagram of the opening operation, and

FIG. 3B shows the block diagram the closing operation.

FIG. 4A shows the block diagram of an impulse filter consisting of an opening operation followed by a closing operation, FIG. 4B shows the block diagram of another impulse filter consisting of a closing operation followed by an opening operation, and FIG. 5 shows yet another block diagram of an impulse filter in which the opening-closing pair and the closing-opening pair operate in parallel.

FIGS. 13A and 13B show example measurement values that result in a peak at P3 of FIG. 13A, but not at P3 of FIG. 13B as P4 is under threshold for a downward trend that would result in a nadir otherwise, so that P5 is designated as a peak as opposed to P3.

DETAILED DESCRIPTION OF THE INVENTION

The following description is of the best mode presently contemplated for carrying out embodiments of the invention. This description is not to be taken in a limiting sense, but is made merely for the purpose of describing the general principles of the invention. The scope of the invention should be determined with reference to the claims.

Embodiments of the invention provide an apparatus and method to extract respiration parameters from a transthoracic impedance signal measured by an implantable medical device. Exemplary respiration parameters or metrics that embodiments of the invention are configured to obtain include but not limited to respiration rate, inspiration/expiration (I/E ratio), tidal volume and minute ventilation for example.

Figure 1A:
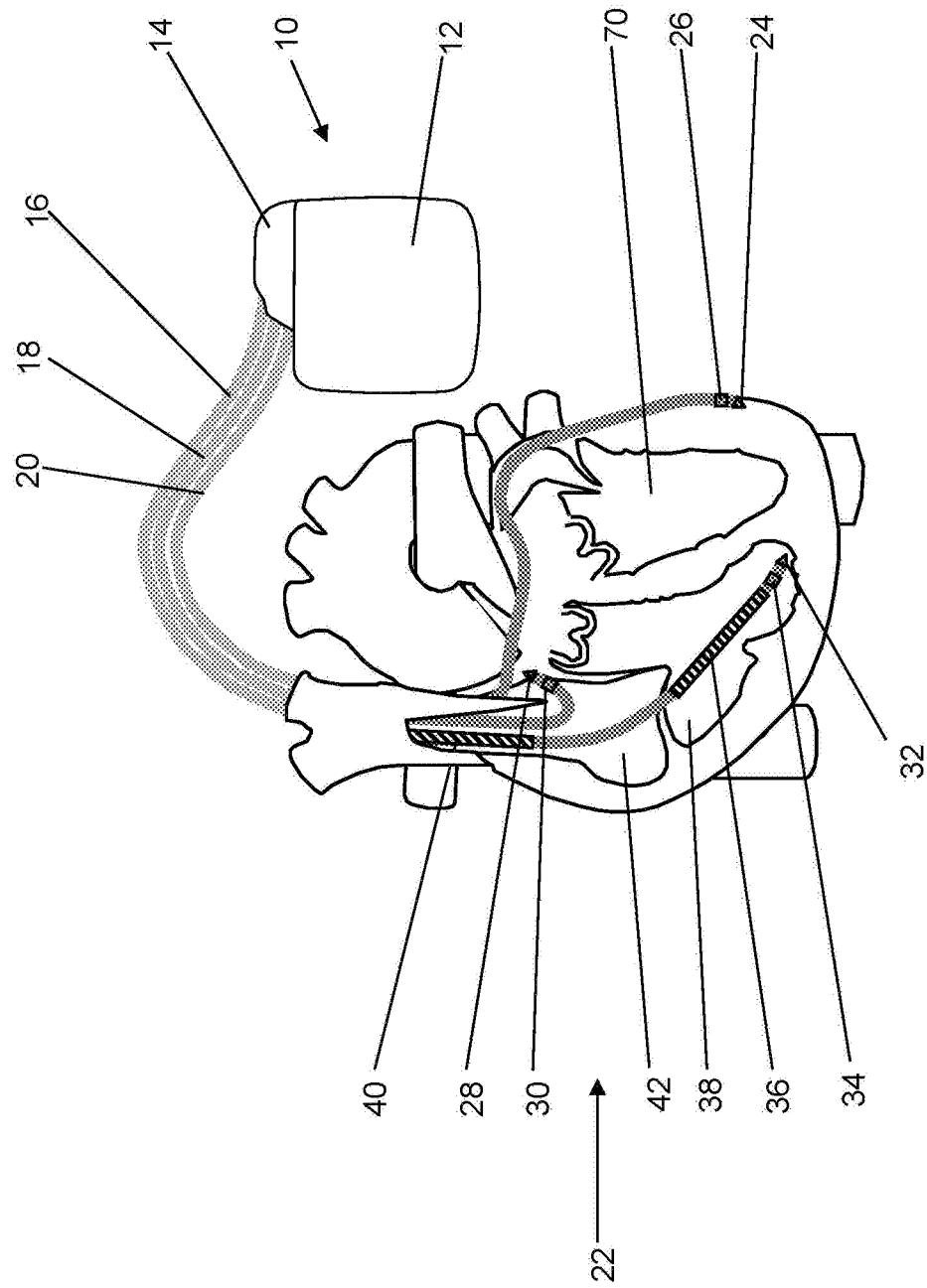
FIG. 1A illustrates the heart stimulator connected to electrode leads that are placed in a heart.

FIG. 1A illustrates an implantable medical device or pacemaker 10, for example a three chamber biventricular pacemaker and cardioverter/defibrillator that is connected to pacing/sensing leads placed in a heart 22.

Pacemaker 10 utilizes a gas proof housing, or "can" 12 made from a biocompatible metal such as titanium. Pacemaker 10 may utilize a transparent header 14 that is made from electrically insulating plastic and that encloses terminals to which electrode leads 16, 18 and 20 are connected detachably. Electrode leads 16, 18 and 20 each comprise a proximal connector (not shown) that is plugged into the connectors of header 14. Thus, implantable medical device 10 is electrically coupled to heart 22 by way of leads 16, 18 and 20.

Lead 18 is a right atrial electrode lead that has a pair of right atrial electrodes 28 and 30 that are in contact with the right atrium 42 of the heart 22.

Lead 16 is a right ventricular electrode lead that has a pair of ventricular stimulation and sensing electrodes 32 and 34 that are in contact with the right ventricle 38 of heart 22. Further, a right ventricular defibrillation shock coil RV-COIL 36 and an atrial defibrillation shock coil SVC-COIL 40 are arranged on lead 16.

Electrodes 28 and 32 are tip electrodes at the very distal end of leads 18 and 16, respectively. Electrode 28 is a right atrial tip electrode RA-TIP and electrode 32 is a right ventricular tip electrode RV-TIP. Electrodes 30 and 34 are ring electrodes in close proximity but electrically isolated from the respective tip electrodes 28 and 32. Electrode 30 forms a right atrial ring electrode RA-RING and electrode 34 forms a right ventricular ring electrode RV-RING. Atrial defibrillation shock coil SVC-COIL 40 and right ventricular defibrillation shock coil RV-COIL 36 are coil electrodes providing a relatively large geometric area when compared to the stimulation electrodes 32, 34, 28 and 30.

Lead 20 is a left ventricular electrode lead passing through the coronary sinus of heart 22 and having a left ventricular ring electrode LV-RING 26 a left ventricular tip electrode LV-TIP 24 in contact with the left ventricle 70 of heart 22.

Implantable medical device 10 has a case or "can" 12 made from electrically conductive material such as titanium that can serve as a large surface electrode IMD CASE.

The plurality of electrodes 32, 34, 28, 30, 24, 26, 36 and 40 connected to implantable medical device 10 together with case 12 allow for a number of different electrode configurations for sensing, pacing, as well as measuring intrathoracic and intracardiac impedance.

Figure 1B:
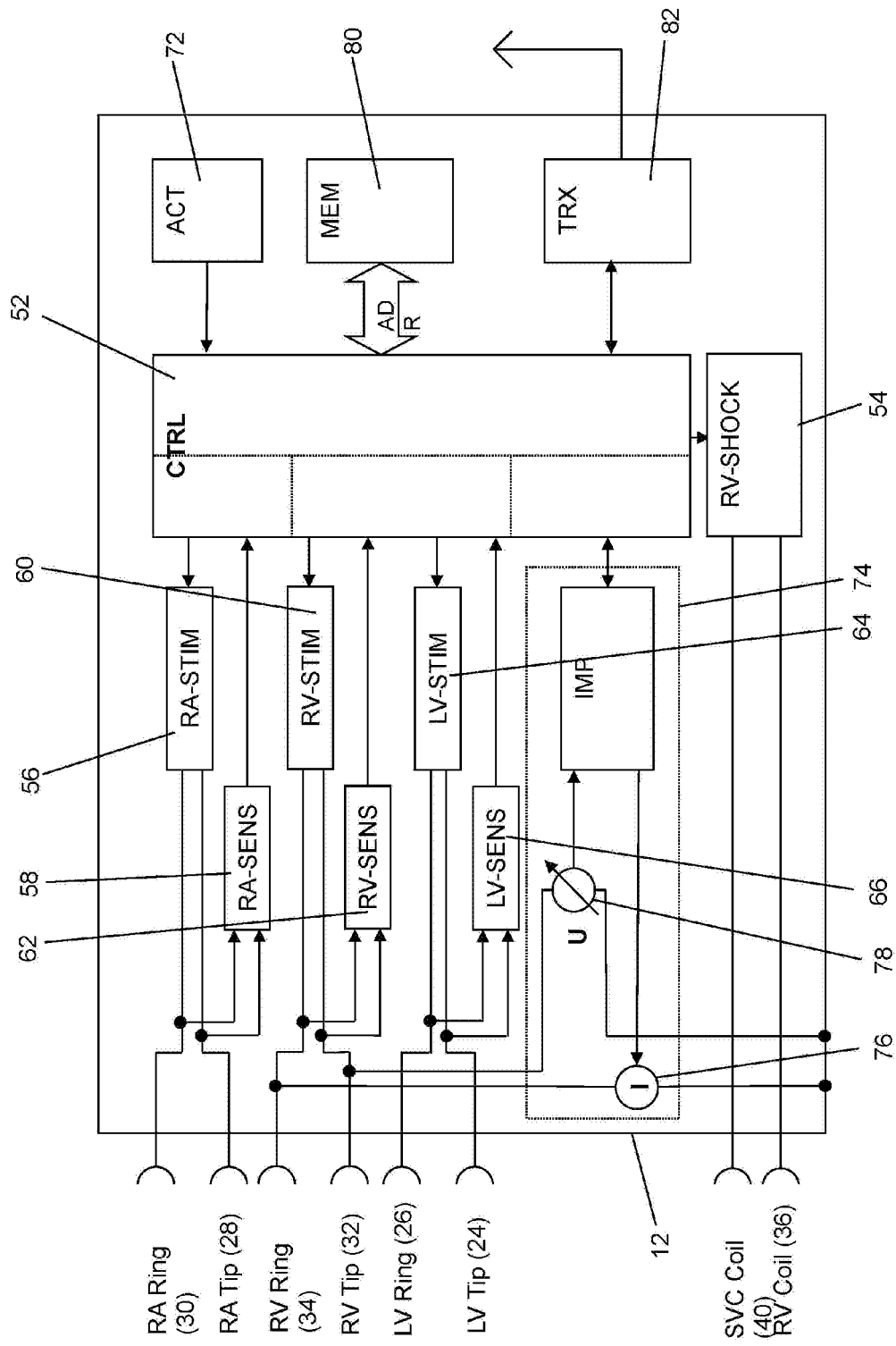
FIG. 1B shows a schematic block diagram of the heart stimulator of FIG. 1A.

Referring to FIG. 1B, a simplified block diagram of an implantable medical device 10 is illustrated. During operation of the pacemaker leads 16, 18 and 20 are connected to respective output/input terminals of pacemaker 10 as indicated in FIG. 1B and carry stimulating pulses to the tip electrodes 32, 28 and 24 from a right ventricular pulse generator RV-STIM 60, a right atrial stimulation pulse generator RA-STIM 56 and a left ventricular pulse generator LV-STIM 64, respectively. On demand, defibrillation pulses will be provided from right ventricular shock generator RV-SHOCK 54, and atrial shock generator RA-SHOCK (not shown for brevity) to right ventricular defibrillation shock coil RV-COIL 36, and an atrial defibrillation shock coil SVC-COIL 40, respectively. Further, electrical signals from the right ventricle are carried from the electrode pair 32 and 34, through the lead 16, to the input terminal of a right ventricular sensing stage RV-SENS 62; and electrical signals from the right atrium are carried from the electrode pair 28 and 30, through the lead 18, to the input terminal of a right atrial channel sensing stage RA-SENS 58. Electrical signals from the left ventricle are carried from the electrode pair 24 and 26, through the lead 20, to the input terminal of a left ventricular sensing stage LV-SENS 66.

The atrial channel sensing stage RA-SENS 58 and ventricular sensing stages RV-SENS 62 and LV-SENS 66 comprise analog to digital converters (ADC; not shown for brevity) that generate digital signals from electric signals picked up in the atrium or the ventricles, respectively.

Controlling the implantable medical device 10 is a control unit CTRL 52 that is connected to sensing stages RA-SENS 58, RV-SENS 62 and LV-SENS 66, to stimulation pulse generators RA-STIM 56, RV-STIM 60 and LV-STIM 64 and to an impedance determination unit 74. Control unit CTRL 54 comprises a digital microprocessor forming a central processing unit (CPU; not shown for brevity) and is, at least in part, controlled by a program stored in a memory circuit MEM 80 that is coupled to the control unit CTRL 54 over a suitable data/address bus ADR.

Control unit CTRL 52 receives the output signals from the atrial sensing stage RA-SENS 58 and from the ventricular sensing stages RV-SENS 62 and LV-SENS 66. The output signals of sensing stages RA-SENS 58 and RV-SENS 62 are generated each time that a P-wave representing an intrinsic atrial event or an R-wave representing an intrinsic ventricular event, respectively, is sensed within the heart 22. An As-signal is generated, when the atrial sensing stage RA-SENS 58 detects a P-wave and a Vs-signal is generated, when the ventricular sensing stage RV-SENS 62 detects an R-wave.

Control unit CTRL 52 also generates trigger signals that are sent to the atrial stimulation pulse generator RA-STIM 56 and the ventricular stimulation pulse generators RV-STIM 60 and LV-STIM 64, respectively. These trigger signals are generated each time that a stimulation pulse is to be generated by the respective pulse generator RA-STIM 56, RV-STIM 60 or LV-STIM 64. The atrial trigger signal is referred to simply as the "A-pulse", and the ventricular trigger signal is referred to as the "V-pulse". During the time that either an atrial stimulation pulse or ventricular stimulation pulse is being delivered to the heart, the corresponding sensing stage, RA-SENS 58, RV-SENS 62 and/or LV-SENS 66, is typically disabled by way of a blanking signal presented to these amplifiers from the control unit CTRL 52, respectively. This blanking action prevents the sensing stages RA-SENS 58, RV-SENS 62 and LV-SENS 66 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

In order to successfully stimulate a heart chamber, a stimulation pulse needs to have strength above capture threshold of that heart chamber. Stimulation pulse strength can be altered by changing the amplitude and/or the pulse with of a stimulation pulse. Control unit CTRL 52 and stimulation pulse generators RA-STIM 56, RV-STIM 60 and LV-STIM 64 are adapted to adjust the pulse strength of stimulation pulses in order to provide stimulation pulses that have a strength sufficient to cause capture, yet without requiring excessive energy in order to avoid unnecessary depletion of the pacemaker's battery.

Control unit 52 is also connected to pulse generators RV-SHOCK 54, LV-SHOCK (not shown for brevity) and optional right atrial shock circuitry if desired (not shown for brevity) to control the delivery of high energy pulses for defibrillation, if necessary.

Control unit CTRL 52 comprises circuitry for timing ventricular and/or atrial stimulation pulses according to an adequate stimulation rate that can be adapted to a patient's hemodynamic need as pointed out below.

Basic timing intervals, among others, are an atrioventricular delay (AV-delay, AVD) between an atrial event and a scheduled right ventricular stimulation pulse and an interventricular delay (VV-delay, VVD) between a right ventricular event and the subsequent left ventricular stimulation pulse, or between a left ventricular event and the subsequent right ventricular stimulation pulse. These and other timing intervals such as an atrial or a ventricular escape interval are controlled by control unit CTRL 54.

Still referring to FIG. 1B, the implantable medical device 10 includes a memory circuit MEM 80 that is coupled to the control unit CTRL 52 over a suitable data/address bus ADR. This memory circuit MEM 80 allows certain control parameters, used by the control unit CTRL 52 in controlling the operation of the implantable medical device 10, to be programmably stored and modified, as required, in order to customize the implantable medical device's operation to suit the needs of a particular patient. Such data includes the basic timing intervals used during operation of the pacemaker 10 and AV delay values and hysteresis AV delay values in particular.

Further, data sensed during the operation of the implantable medical device 10 may be stored in the memory MEM 80 for later retrieval and analysis.

A telemetry circuit TRX 82 is further included in the implantable medical device 10. This telemetry circuit TRX 82 is connected to the control unit CTRL 52 by way of a suitable command/data bus. Telemetry circuit TRX 82 allows for wireless data exchange between the implantable medical device 10 and an external device or some remote programming or analyzing device which can be part of a centralized service center serving multiple pacemakers.

The implantable medical device 10 in FIG. 1B is referred to as a three chamber pace-maker/cardioverter/defibrillator because it interfaces with the right atrium 42, the right ventricle 38 and the left ventricle 70 of the heart 22. Those portions of the pacemaker 10 that interface with the right atrium 42, e.g., the lead 18, the P-wave sensing stage RA-SENSE 58, the atrial stimulation pulse generator RA-STIM 56 and corresponding portions of the control unit CTRL 52, are commonly referred to as the atrial channel. Similarly, those portions of the pacemaker 10 that interface with the right ventricle 38, e.g., the lead 16, the R-wave sensing stage RV-SENSE 62, the ventricular stimulation pulse generator RV-STIM 60, and corresponding portions of the control unit CTRL 52, are commonly referred to as the right ventricular channel. Likewise, those portions of the pacemaker 10 that interface with the left ventricle 70, e.g. the lead 20, the sensing stage LV-SENS 66, the left ventricular stimulation pulse generator LV-STIM 64, and corresponding portions of the control unit CTRL 52, are commonly referred as the left ventricular channel.

In order to be able to detect periods of physical activity of a patient indicating that the patient is awake and in order to allow rate adaptive pacing in a DDDR or a DDIR mode, the pacemaker 10 further includes a physiological sensor ACT 72 that is connected to the control unit CTRL 52 of the pacemaker 10. While this sensor ACT 72 is illustrated in FIG. 1B as being included within the pacemaker 10, it is to be understood that the sensor may also be external to the implantable medical device 10, yet still be implanted within or carried by the patient. A common type of sensor is an accelerometer, such as a piezoelectric crystal, mounted to the case of the pacemaker. Other types of physiologic sensors are also known, such as sensors that sense the oxygen content of blood, respiration rate, blood pH, intra-cardiac impedance changes, and the like. The type of sensor used is not critical to the present invention. Any sensor capable of sensing some physiological parameter relatable to physical activity of a patient can be used. Such sensors are commonly used with "rate-responsive" pacemakers in order to adjust the rate of the pacemaker in a manner that tracks the physiological needs of the patient.

The control unit CTRL 52 is adapted to determine an adequate heart rate or stimulation rate in any manner known as one skilled in the art will appreciate.

For impedance measurement, an impedance determination unit 74 is provided. Impedance determination unit 74 comprises a constant current source 76 that is connected or can be connected to electrodes for intracorporeal placement as shown in FIG. 1. In order to allow for a plurality of impedance measurement electrode configurations, some means of switching may be provided between the constant current source 76 and the electrode terminals of the implantable medical device 10. The switch is not shown in FIG. 1B. Rather, particular impedance measurement configurations are shown as examples.

Similarly, an impedance measuring unit 78 for measuring a voltage corresponding to a current fed through a body by said constant current source is provided and can be connected to a number of electrodes although a switch for switching between these configurations is not shown in FIG. 1B.

As an alternative to constant current source 76 a constant voltage source can be provided. Then, the measuring unit will be adapted to measure a current strength of a current fed through a body by said constant voltage source.

Both, constant current source 76 and impedance measurement unit 78, are connected to an impedance value determination unit IMP that is adapted to determine an impedance value for each measuring current pulse delivered by the constant current source 76.

The impedance value determination unit IMP comprises another analog to digital converter ADC in order to generate a digital impedance signal that is fed to the control unit CTRL 52.

Control unit CTRL 54 further comprises watchdog and reset units (not shown) to provide safety when the CPU should fail. The watchdog units therefore are designed to operate independently from the CPU of the control unit CTRL 54.

Figure 1C:
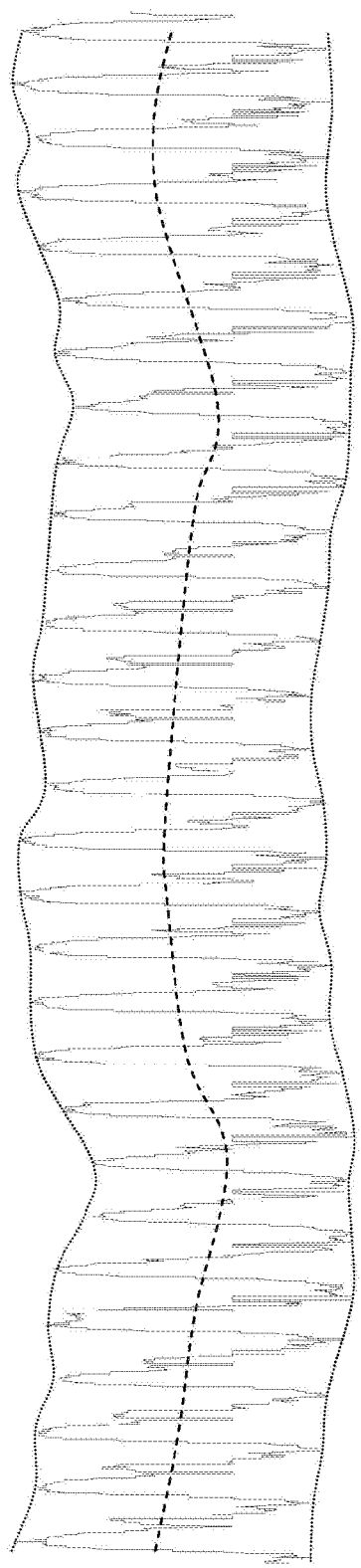
FIG. 1C shows a typical time course of transthoracic impedance measurements further illustrated to show the cardiac and respiratory components as obtained via the hardware shown in FIGS. 1A-B.

FIG. 1C shows a typical time course of transthoracic impedance measurements further illustrated to show the cardiac and respiratory components. Transthoracic impedance signal (Z) has both cardiac component (Zc) and the respiratory component (Zr). The Zc is associated with the mechanic activity of the heart (contraction and relaxation), whereas Zr is associated with the mechanic activity of the lung (inhalation and exhalation). As shown, each cardiac beat correspond to one cycle of Zc, which starts from a valley to the following peak then returns to the next valley of the impedance waveform. On the other hand, the respiratory cycles are tracked by the Zr component which corresponds to the trend of the impedance waveform (dashed lines) as well as the envelopes of the Zc peaks and nadirs (dotted lines). Generally, the dominant frequency of Zr is much lower than that of Zc. The transthoracic impedance increases during inspiration as more air fills the lung and decreases during expiration as air is expelled out of the lung.

As known in the art, the impedance signal also provides useful information on the integrity of the sensing channel. In addition, the continuously measured impedance signal may be further processed by the control unit CTRL 52 to extract other physiological status of the patient, such as the respiration rate as is described in further detail below.

Other types of biological signals measured by specific sensors can also serve as input to the implant device 10. For example, an on-board accelerometer can serve as a motion sensor in activity monitor ACT 72 that provides patient's activity signal to the implant device 10, an on-board (or embedded in the lead) temperature sensor for example that can provide the subcutaneous temperature signal to the implant device 10. Other types of input signals include, but are not limited to, the pressure signal measured by a pressure sensor, the acoustic signal measured by an acoustic sensor, the subcutaneous pH signal measured by a pH sensor, etc.

By running the program stored in the memory 80, the control unit also sends instructions the impedance measurement unit 74, and other input measurement units to control how these signals are acquired (e.g., gain, offset, filter settings, sampling frequency, sampling resolution, etc.).

The acquired biological signals are then stored in memory 80 and analyzed by the control unit by running programmed algorithms. For example, the control unit may continuously obtain and analyze the transthoracic impedance to determine respiration parameters and/or also obtain and analyze the acquired ECG signals to detect the peak of QRS complex as is taught in the parent application to which the instant application claims priority to and also which has been incorporated by reference herein. Such QRS peak detection can be achieved by many different means. In another embodiment, the QRS peak detection is achieved by using an Auto-Sensing algorithm that automatically adjust the sensing threshold, which is adaptive to the measured peak amplitude of the QRS complex and varies based on a predetermined time dependence. One exemplary Auto-Sensing algorithm has been disclosed in U.S. Pat. No. 5,891,048, assigned to the present assignee.

The implant device 10 also includes a radio-frequency (RF) telemetry unit TRX 82. The RF telemetry unit TRX 82 may be of the type well known in the art for conveying various information which it obtains from the implant device 10, for example to an optional external programmer (not shown for brevity), or for receiving programming parameters from the optional external programmer and then conveys to the implant device 10. In one typical embodiment, the optional external programmer can interrogate the implant device 10 to get the status of the implant device 10 (e.g., battery status, sensing channel impedance, etc.) or the data recorded by the implant device 10 (e.g., respiration parameters, peak amplitude of the QRS complexes, statistics of measured RR intervals, etc.). In another typical embodiment, the optional external programmer can be used to activate or deactivate selected algorithms or update programmable parameters of the implant device 10 as one skilled in the art will appreciate. Embodiments of the invention may also interact with external portable devices or one or more remote service center as one skilled in the art will appreciate and which is taught in the parent application to the instant application, and which is incorporated herein by reference.

The method to detect respiratory metrics from transthoracic impedance using morphological operators is disclosed hereinafter.

In one or more embodiments of the invention, the implant device continuously or in desired time windows measures the transthoracic impedance signal (Z), which is band pass filtered (e.g. with high-pass corner frequency 0.4 Hz and low-pass corner frequency 40 Hz) and digitally sampled (e.g. with sampling frequency 128 Hz). Also according to embodiments of the invention, morphological operators are implemented, either in embedded software or in the hardware platform of the device 10, for example as programmed to execute on microprocessor 20. As described in detail later, these morphological operators are applied to the measured transthoracic impedance signal (Z), to remove the cardiac component (Zc) while retaining the respiratory component (Zr) of Z.

Now the concept of morphological operators is described. There are two basic morphological operators: erosion and dilation. These basic operators are usually applied in sequence that yields two derived morphological operations: opening and closing.

Denote $F=[f_0, f_1, \ldots, f_{N-1}]$ the discrete input signal, and denote $K=[k_0, k_1, \ldots, k_{M-1}]$ a predefined discrete kernel function, also called structure element (SE), where N and M are two integers that N>M.

The erosion of the signal F by the structure element K, denoted $F \ominus K$, is defined as:

$$F \ominus K(i) = \min_{j=0, \ldots, M-1} f_{i+j} - k_j$$

for $i = 0, 1, \ldots, N - M$

The erosion is a shrinking operation in that values of $F \ominus K$ are always less than those of F if all elements of the SE are greater than zero. FIG. 2A shows the circuit block diagram of implementing the erosion operator. The input signal passes through a cascade of delay units 100, 100' and 100". The structuring elements 102, 102' and 102" and 102'" are subtracted from the input samples with corresponding delay taps 104, 104', 104" and 104'". For each snapshot of the input signal with segment length M, one output sample is generated, by finding the minimum 106 of the subtracted values. Note that compared to the input signal, the erosion output is delayed by M−1 taps. Also note that if SE is an all zero vector, then the subtraction operation is not needed.

The dilation of the signal F by the structure element K, denoted $F \oplus K$, is defined as:

$$F \ominus K(i) = \max_{j=i-M+1, \ldots, i} f_j + k_{i-j}$$

for $i = M - 1, M, \ldots, N - 1$

The dilation is an expansion operation in that values of $F \oplus K$ are always larger than those of F if all elements of the SE are greater than zero. FIG. 2B shows the circuit block diagram of implementing the dilation operator. The input signal passes through a cascade of delay units 150, 150' and 150". The structuring elements 152, 152' and 152" and 152'" are reversed and then added to the input samples with corresponding delay taps 154, 154', 154" and 154'". For each snapshot of the input signal with segment length M, one output sample is generated, by finding the maximum 156 of the added values. Note that compared to the input signal, the dilation output has no time delay. Also note that if SE is an all zero vector, than the addition operation is not needed.

As illustrated in FIG. 3A, opening of a data sequence by a SE is defined as erosion 202 followed by a dilation 204. The opening of a data sequence can be interpreted as sliding the SE along the data sequence from beneath and the result is the highest points reached by any part of the SE. As further illustrated in FIG. 3B, closing of a data sequence by a SE is defined as dilation 204' followed by an erosion 202'. The closing of a data sequence can be interpreted as sliding a 'flipped-over' version of the SE along the data sequence from above and the result is the lowest points reached by any part of the SE.

In typical applications, opening is used to suppress peaks while closing is used to suppress pits. Therefore, in order to suppress both peaks and pits, opening and closing are usually used in pairs. For example, FIG. 4A shows the block diagram of an impulse filter that removes both peaks and pits by applying an opening operation 302 followed by a closing operation 304. Similarly, FIG. 4B shows the block diagram of another impulse filter by applying a closing operation 304' followed by an opening operation 302'. FIG. 5 shows yet another block diagram of an impulse filter that combines the previous two filters. In this case, the opening-closing pair (302" and 304") and the closing-opening pair (304'" and 302'") operate in parallel, and their outputs are averaged (306) to generate the filtered output.

The design of the SE depends on the shape of the signal that is to be preserved. A SE is characterized by its shape, width, and height. It has been demonstrated that the width of the SE plays a more important role, compared to either the height or the shape, in determining the impulse suppression performance. In the following description of the embodiments of the invention, the SE is considered as an all zero vector with predefined width, although one skilled in the art will appreciate that other types of SE can be defined. To remove Zc and preserve Zr in the transthoracic impedance signal, the width of SE is preferably set to be longer than the cardiac cycle length but shorter than the respiratory cycle length.

Figure 6:
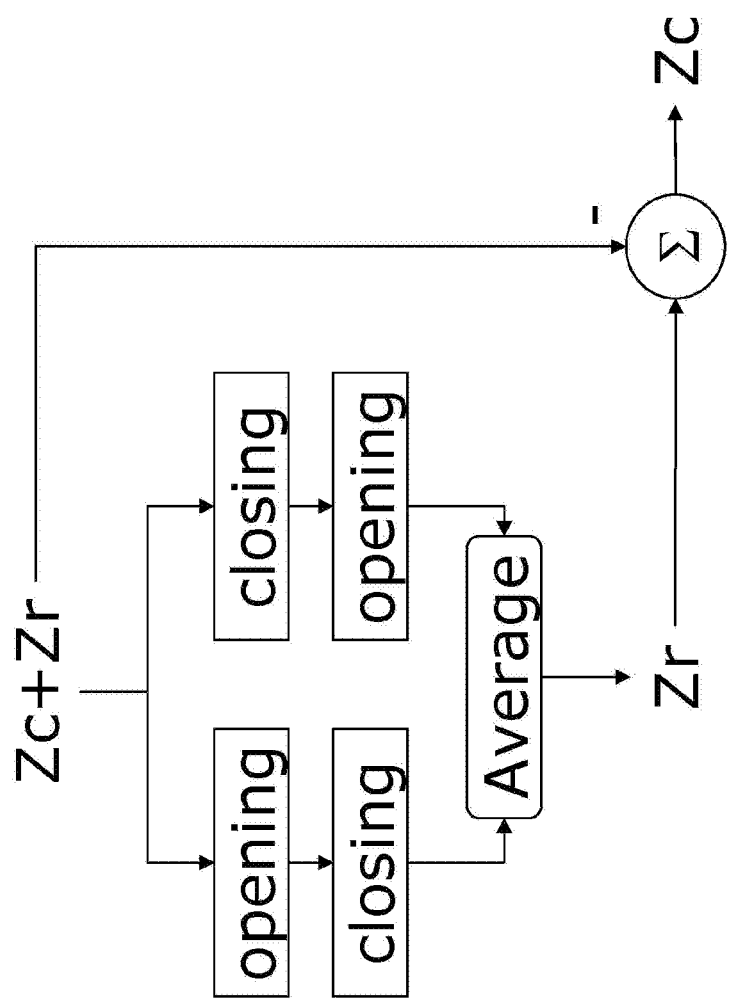
FIG. 6 shows the block diagram of applying a morphological impulse filter to the input intrathoracic impedance signal to obtain the filtered respiration impedance signal and the cardiac impedance signal.

FIG. 6 shows yet another design of impulse filter that combines the previous two filters. In this case, the opening-closing pair and the closing-opening pair operate in parallel, and their outputs are averaged to generate the filtered output. According to this invention, the input signal is the transthoracic impedance signal (Z) that is composed of both cardiac component (Zc) and the respiratory component (Zr). Because Zc can be viewed as embedded impulses and Zr can be viewed as the trend of Z, the impulse filter shown in FIG. 6 is designed to remove the Zc component while preserving the Zr component in the output. By subtracting Zr from the original Z signal, the Zc component can also be extracted.

According to one embodiment of this invention, the width of SE is user-programmable or selectable from a predetermined range. In an exemplary embodiment, the width of SE is set to correspond to about 2-second duration. For example, when the sampling frequency of Z is 128 Hz, the width of SE can be set to 255. According to another embodiment of this invention, the width of SE is dynamically adjusted based on the heart rate. For example, the width of the SE can be set to:

$$\min(W_{max}, \max(W_{min}, K \times CL + d))$$

where K is user-programmable or selectable from a predetermined range (e.g. from 2 to 5), CL is the mean cardiac cycle length expressed as the number of samples over the previous N heart beats (e.g. N=8), d is a predefined offset constant (e.g. d=−1), $W_{min}$ is the lower boundary of SE width (i.e. the shortest SE width allowed at high heart rate), and $W_{max}$ is the upper boundary of SE width (i.e. the longest SE width allowed at low heart rate).

Figure 7:
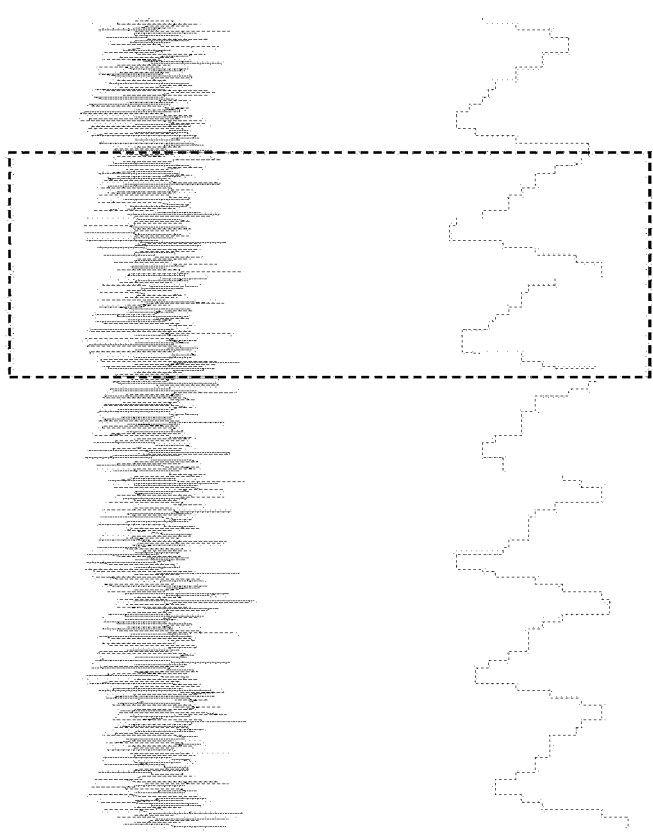
FIG. 7 shows an example of a segment of transthoracic impedance signal measured by the implantable device, together with the filtered respiration impedance signal after applying the morphological filter shown in FIG. 6.

FIG. 7 shows an example of using the morphological operators to extract the Zr component from the Z signal. The top trace shows the transthoracic impedance that includes both Zc component evidenced by narrow spikes and Zr component evidenced by the low-frequency modulation of the Z waveform. The bottom trace shows the extracted Zr component which correlates with the trend of the Z waveform.

Figure 8:
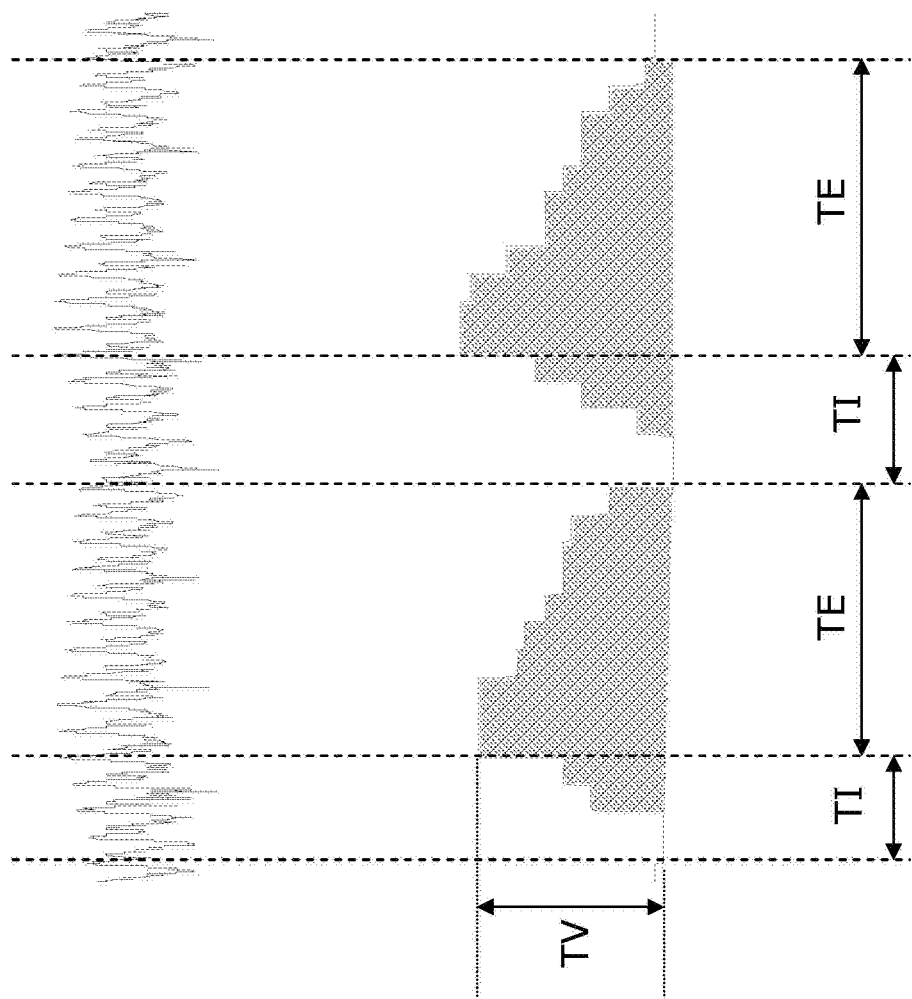
FIG. 8 shows a close-up of the portion of FIG. 7 in dashed lines, specifically showing the tidal volume (TV), inspiration time (TI) and expiration time (TE) metrics extracted from the transthoracic impedance signal after filtering with morphological operators to generate the filtered impedance signal in the lower portion of the figure.

FIG. 8 shows the zoom-in view of two respiratory cycles that are marked by the dashed box in FIG. 7). The Zc component is represented by Z complexes that occur every cardiac cycle, whereas the Zr component is evident from the envelope of the Zc peaks and nadirs. From the extracted Zr component, a plural of respiratory metrics can be measured. For example, the duration of the inspiration time (TI) can be measured from the nadir of a Zr component to the following peak of the Zr component, and the duration of the expiration time (TE) can be measured from the peak of a Zr component to the following nadir of the Zr component. Therefore, the instantaneous respiratory cycle length can be calculated as TI+TE, and the instantaneous respiratory rate can be calculated as 1/(TI+TE). The instantaneous inspiration/expiration (I/E) ratio can be calculated as TI/TE. In addition, the difference between the peak and nadir of each Zr component represents the tidal volume (TV) of that respiratory cycle. As shown, the mean respiratory cycle length, the mean respiratory rate, the mean I/E ratio, and the mean TV can be calculated over a period of time that includes multiple respiratory cycles. Moreover, the area under the Zr component, as illustrated by the shaded area in FIG. 8, represents the volume of gas ventilated for each respiratory cycle. Hence the integration of the area under the Zr component over one minute corresponds to the minute ventilation.

Figure 9:
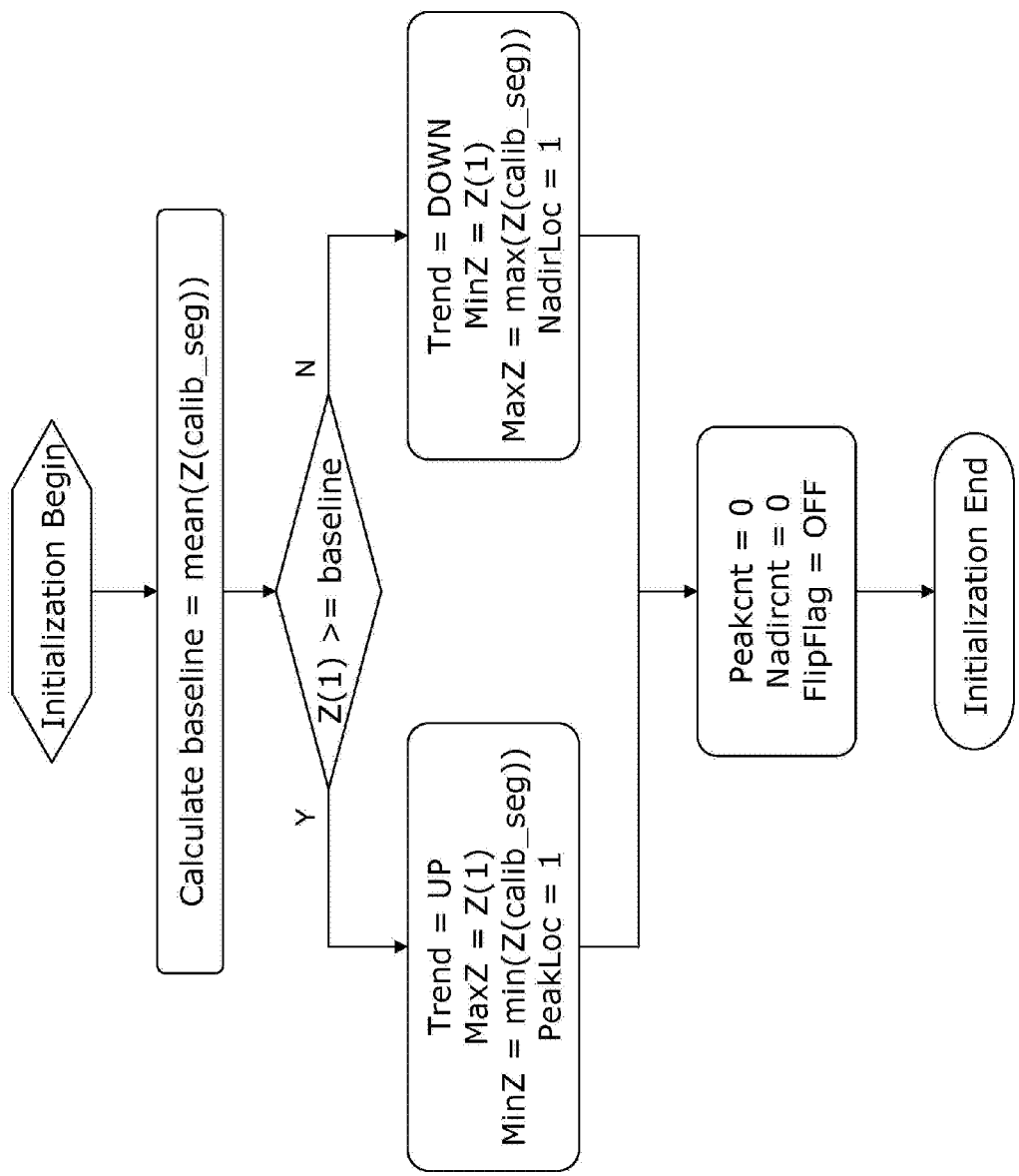
FIG. 9 shows a flow chart for initialization of peak-nadir detection algorithm.

FIG. 9 shows a flow chart for initialization of processing of the filtered impedance signal that represents the Zr component. A baseline is initially calculated as the average of the filtered impedance of a calibration segment and if the first impedance value is greater than or equal to the baseline, then processing continues on the left portion of the flow chart. The variable Trend (a flag) is labelled as "UP". The variable MaxZ is set to the first impedance value and the variable MinZ is set to the minimum value of the impedance that occurs in the calibration segment. The PeakLoc flag is set to 1 (true) since the first value is higher than the baseline, or at least equal thereto. If the first impedance value is less than the baseline, then processing continues on the right side of the flow chart. The variable Trend (a flag) is labelled as "DOWN". The variable MinZ is set to the first impedance value and the variable MaxZ is set to the maximum value of the impedance that occurs in the calibration segment. The NadirLoc flag is set to 1 (true) since the first value is lower than the baseline. Initial values for peak count (Peakcnt), nadir count (Nadircnt) and flip flag (FlipFlag) are respectively set and initialization is complete.

Figure 10:
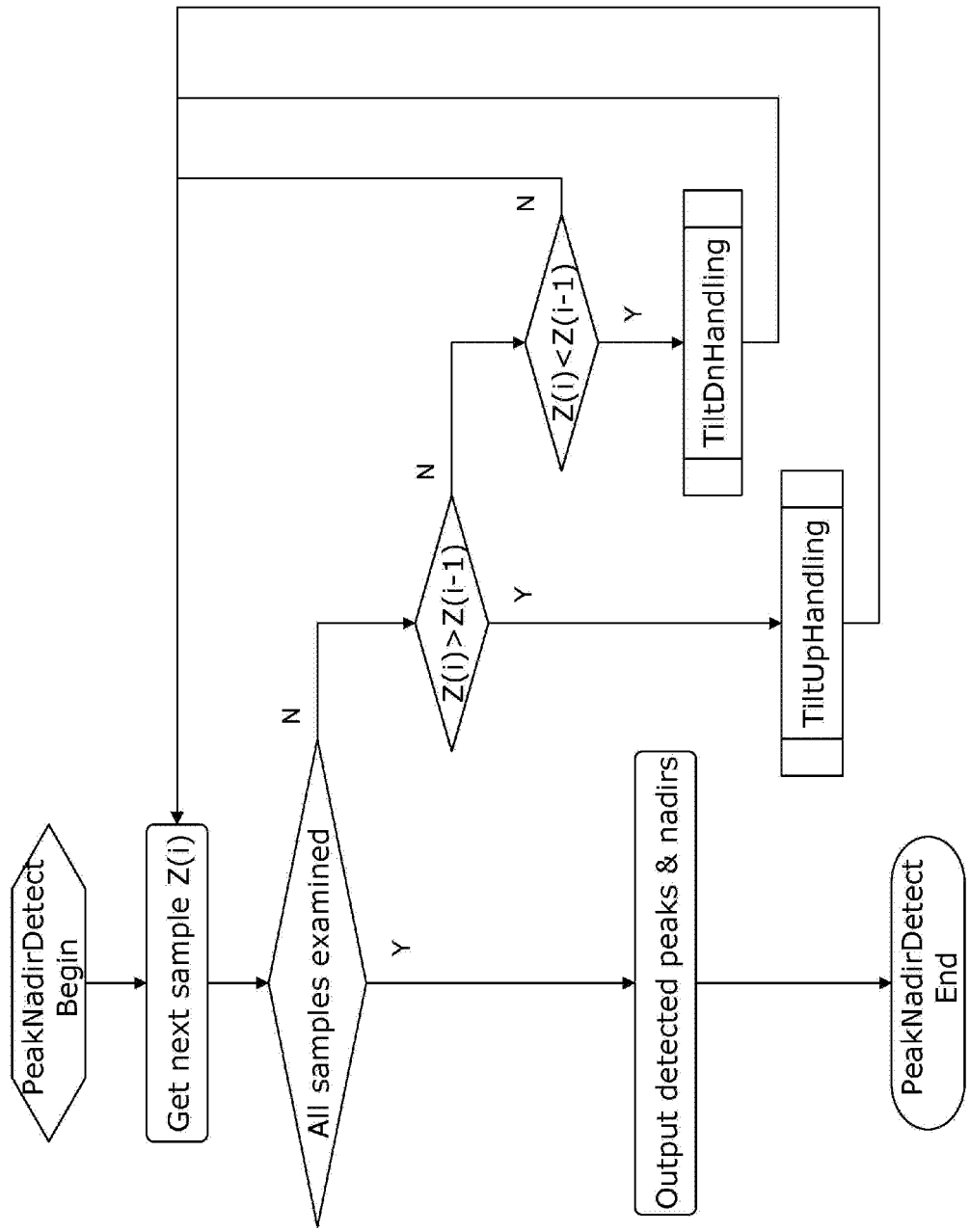
FIG. 10 shows a flow chart for the peak and valley or nadir detection used to calculate metrics based on the morphologically filtered impedance data, for example as shown in the lower portion of FIG. 8.

FIG. 10 shows a flow chart for the peak and valley or nadir detection used to calculate metrics based on the morphologically filtered impedance data, for example as shown in the lower portion of FIG. 8 and which represents the Zr component. As shown, each impedance value is obtained and if all samples have been examined, then the output of the detected peaks and nadirs occurs and processing ends. The process may begin again or loop forever if desired. If there are more samples to examine, then if the impedance of the current sample Z(i) is greater than the impedance of the previous sample Z(i−1), then "TiltUpHandling" processing occurs. If Z(i) is less than Z(i−1) then "TiltDnHandling" processing occurs. Otherwise, the current sample Z(i) is equal to the previous sample Z(i−1) and hence there is no up or down motion to the samples, so the next sample is obtained and processing through the loop continues again.

Figure 11:
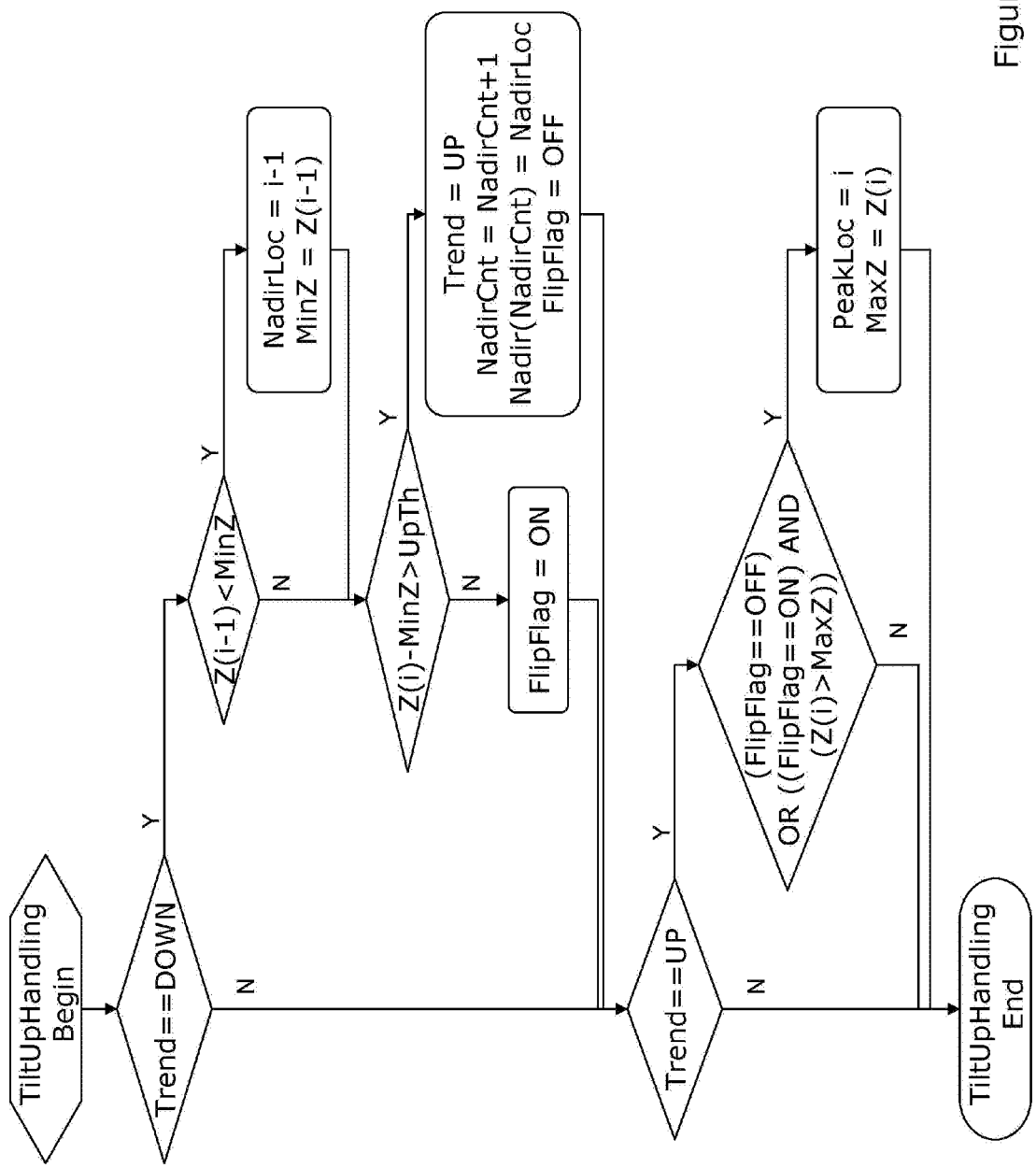
FIG. 11 shows the detail of the "TiltUpHandling" processing of FIG. 10.

FIG. 11 shows the detail of the "TiltUpHandling" processing of FIG. 10. This is the path taken when the current value is greater than the previous value, for example for points P2 and P3 of FIG. 13A, P2, P3, and P5 of FIG. 13B, P4 of FIG. 14A and P4 and P6 of FIG. 14B.

Figure 12:
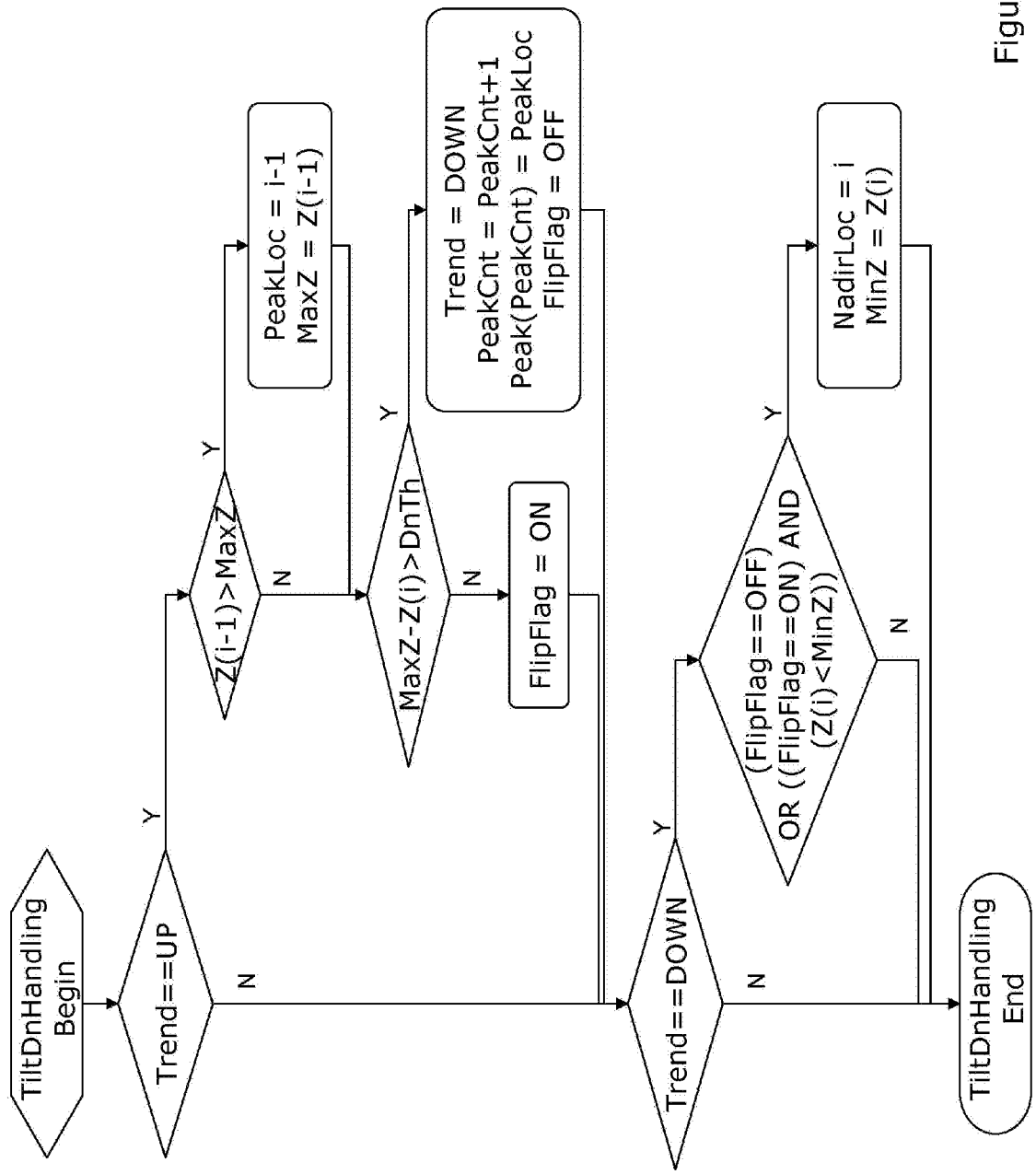
FIG. 12 shows the detail of the "TiltDnHandling" processing of FIG. 10.

FIG. 12 shows the detail of the "TiltDnHandling" processing of FIG. 10. This is the path taken when the current value is less than the previous value, for example for points P4 of FIG. 13A, P4 and P6 of FIG. 13B, P2 and P3 of FIG. 14A and P2, P3 and P5 of FIG. 14B.

Processing is as follows: If a current value is greater than the previous value, then "TiltUpHandling" routine is entered. On entry, a test to determine if the general "Trend" flag had been set to "DOWN" is performed. If the Trend flag had previously been set to "DOWN", this would signify a change in direction of the values. A value of "DOWN" means that the previous main direction of the sequence of values was decreasing, or at least not rising over a threshold. If the Trend had been set to "UP" on entry, then the values are continuing to rise. In this case, as is the case for value P2 of FIG. 13A, then the Peak Location is set to the current index of P2, and the MaxZ value is set to the value of P2 since the FlipFlag is initially "OFF". This continues at P3 of FIG. 13A wherein the Trend is "UP" and the FlipFlag is still set to "OFF". When value P4 of FIG. 13A is obtained (as per the flow chart of FIG. 10), then the "TiltDnHandling" routine is entered. The Trend was "UP", so the top portion of the flow chart is entered, wherein the P3 value was equal to the MaxZ, so that the threshold check is performed. If the decrease in value exceeds the Down Threshold "DnTh", then the Trend is set to "DOWN", the parameters of the Peak are set (e.g. peak count is increased by one and peak location is marked), and FlipFlag remains as OFF. On the other hand, for example in the case of FIG. 13B, if the difference between P4 and P3 (the MaxZ up to that point) is not over the threshold, then the FlipFlag is set to "ON" and this does not change Trend to "DOWN", but rather considers P4 as an under-threshold move which does not warrant a downward trend designation. In the case of P5 of FIG. 13B, the "TiltUpHandling" routine is entered. Trend "UP" processing where the FlipFlag is "ON" and the value of P5 is greater than P3 sets the peak location and maximum value to the index of P5 and value of P5 without setting a nadir at P4.

Figure 14:
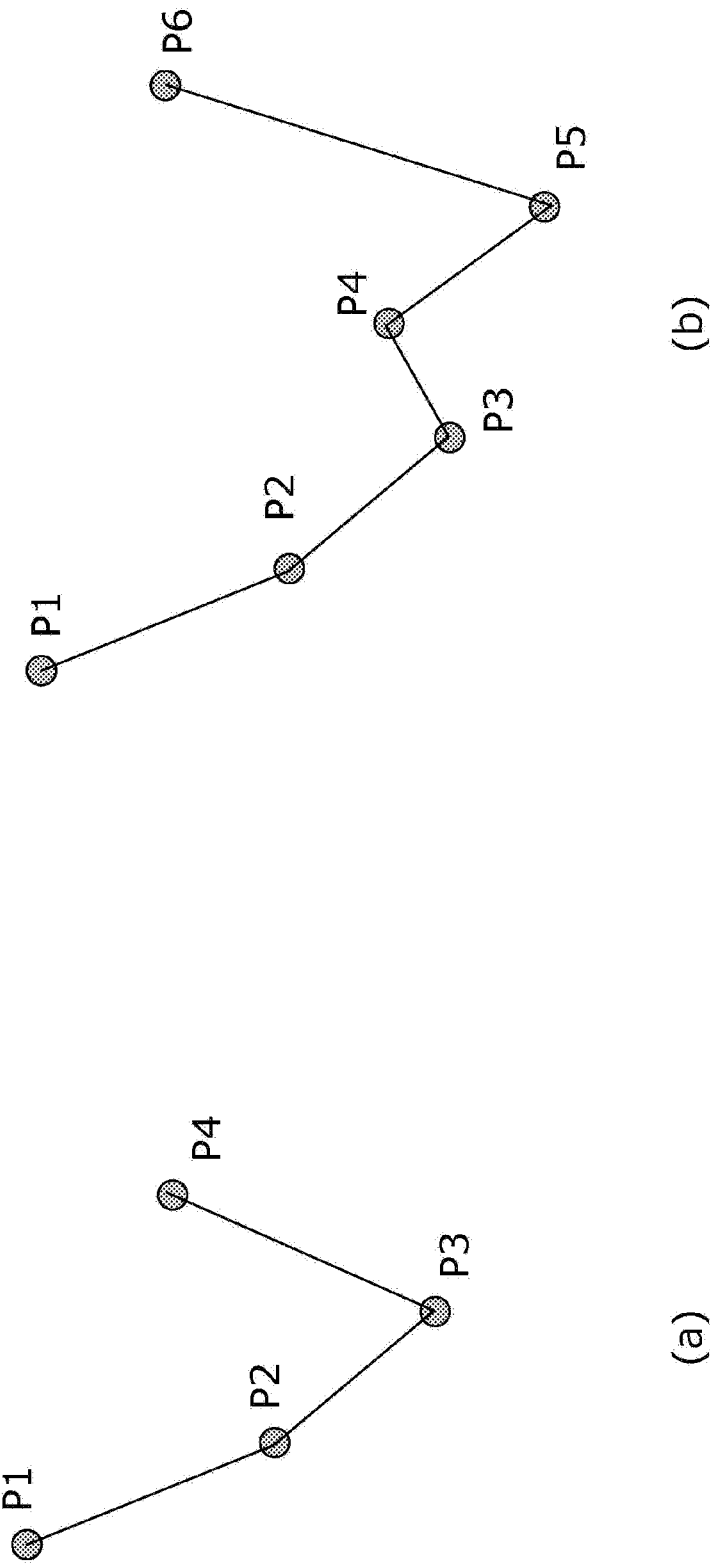
FIGS. 14A and 14B show example measurement values that result in a nadir at P3 of FIG. 14A, but not at P3 of FIG. 14B as P4 is under threshold for an upward trend that would result in a peak otherwise, so that P5 is designated as a nadir as opposed to P3.

If a current value is less than the previous value, then "TiltDnHandling" routine is entered. On entry, a test to determine if the general "Trend" flag had been set to "UP" is performed. If the Trend flag had previously been set to "UP", this would signify a change in direction of the values. A value of "UP" means that the previous main direction of the sequence of values was increasing, or at least not decreasing over a threshold. If the Trend had been set to "DOWN" on entry, then the values are continuing to decrease. In this case, as is the case for value P2 of FIG. 14A, then the Nadir Location is set to the current index of P2, and the MinZ value is set to the value of P2 since the FlipFlag is initially "OFF". This continues at P3 of FIG. 14A wherein the Trend is "DOWN" and the FlipFlag is still set to "OFF". When value P4 of FIG. 14A is obtained (as per the flow chart of FIG. 10), then the "TiltUpHandling" routine is entered. The Trend was "DOWN", so the top portion of the flow chart is entered, wherein the P3 value was equal to the MinZ, so that the threshold check is performed. If the increase in value exceeds the Up Threshold "UpTh", then the Trend is set to "UP", the parameters of the Nadir are set (e.g. nadir count is increased by one and nadir location is marked), and FlipFlag remains as OFF. On the other hand, for example in the case of FIG. 14B, if the difference between P4 and P3 (the MinZ up to that point) is not over the threshold, then the FlipFlag is set to "ON" and this does not change Trend to "UP", but rather considers P4 as an under-threshold move which does not warrant an upward trend designation. In the case of P5 of FIG. 14B, the "TiltDnHandling" routine is entered. Trend "DOWN" processing where the FlipFlag is "ON" and the value of P5 is less than P3 sets the nadir location and minimum value to the index of P5 and value of P5 respectively without setting a peak at P4.

Figure 15:
FIG. 15 shows detection of respiration signal along with the transthoracic impedance values wherein triangles show changes in trends, for example peaks and nadirs as opposite pointing triangles for example.

FIG. 15 shows detection of respiration signal along with the transthoracic impedance values wherein triangles show changes in trends. As shown peaks and nadir locations are shown as upward and downward pointing triangles respectively as set by the processing performed via the flowcharts of FIGS. 10, 11 and 12 and as programmed in microprocessor 20 as one skilled in the art will appreciate. The device 10 stores the measured respiratory metrics, including the respiratory rate, tidal volume, I/E ratio, minute ventilation, etc., based on the calculation of the peaks and nadirs for example. These metrics can be interrogated by the external programmer during follow-up, or can be transmitted automatically through Home Monitoring network. These measured respiratory metrics can assist acute detection of respiratory abnormalities such as sleep apnea, or facilitate long-term monitoring and diagnosis of disease progressions such as heart failure.

Although the above embodiment is described as extracting the respiratory signal from the transthoracic impedance waveform, it should be understood that the same method may be applied to extract the respiratory signal from the intracardiac impedance signal, or wide-band cardiac electrogram such as the surface ECG or far-field intracardiac electrogram, which are also modulated by the respiration.

Embodiments of the invention provide a novel means of extracting respiration signal from the transthoracic impedance signal. Compared to conventional filter design methods, the morphological filter has better performance in removing the cardiac components while preserving the respiratory component in terms of accuracy and computation complexity.

Although an exemplary embodiment of the invention has been shown and described, it should be apparent to those of ordinary skill that a number of changes and modifications to the invention may be made without departing from the spirit and scope of the invention. All such changes, modifications and alterations should therefore be recognized as falling within the scope of embodiments of the invention described herein.

What is claimed is:

1. A heart monitor configured to obtain respiration metrics comprising:
an impedance signal input;
an impedance measurement unit coupled with said impedance signal input;
a microprocessor configured to obtain a first time series of values that represent a transthoracic impedance signal obtained from said impedance measurement unit; and, said microprocessor further configured to
generate a modified time series of values that represent a trend of values of said first time series through application of at least one morphological operator comprising
an erosion operator or
a dilation operator or
any combination thereof
wherein said trend of values comprises a respiratory component of said first times series, and
wherein said at least one morphological operator includes said erosion operator defined by $$F \ominus K(i) = \min_{j=0,\ldots,M-1} f_{i+j} - k_j$$

for $i = 0, 1, \ldots, N - M$ and also includes said dilation operator defined by $$F \odot K(i) = \max_{j=i-M+1,\ldots,i} f_j + k_{i-j}$$

for $i = M - 1, M, \ldots, N - 1$ where $F=[f_0, f_1, \ldots, f_{N-1}]$ is a discrete input signal comprising said first time series, and where $K=[k_0, k_1, \ldots, k_{M-1}]$ is a predefined discrete kernel function, or structure element or SE, and where N and M are two integers that N>M and where M is set dynamically to $$\min(W_{max}, \max(W_{min}, K \times CL + d))$$

where K is user-programmable or selectable from a predetermined range, CL is the mean cardiac cycle length expressed as the number of samples over the previous H heart beats where H is a predefined positive integer, d is a predefined offset constant, $W_{min}$ is the lower boundary of SE width, and $W_{max}$ is the upper boundary of SE width.

2. The heart monitor of claim 1, wherein said microprocessor is further configured to subtract said first time series from said modified time series and to thus generate a cardiac component of said first times series.

3. The heart monitor of claim 1, wherein said microprocessor is configured to generate said modified time series through application of both an opening operator and a closing operator to said first time series to thus obtain said modified time series of values that represent the trend of values of said first time series.

4. The heart monitor of claim 3, wherein said microprocessor is configured to generate said modified time series through application of said erosion operator followed by said dilation operator that together form the opening operator to suppress peaks in the first time series.

5. The heart monitor of claim 3, wherein said microprocessor is configured to generate said modified time series through application of said dilation operator followed by said erosion operator that together form the closing operator to suppress pits in the first time series.

6. The heart monitor of claim 1, wherein K is a vector comprising all zeroes.

7. The heart monitor of claim 1, wherein M comprises enough values to cover a time period longer than a cardiac cycle length but shorter than a respiratory cycle length.

8. The heart monitor of claim 1, wherein said trend of values comprises a respiratory component that is measured from a nadir to a following peak to determine inspiration time (TI) and wherein said trend of values is calculated to disregard under-threshold moves in a direction opposite to a current up or down trend of values.

9. The heart monitor of claim 1, wherein said trend of values comprises a respiratory component that is measured from a peak to a following nadir to determine expiration time (TE).

10. The heart monitor of claim 1, wherein said trend of values comprises a respiratory component that is measured by adding time from a nadir to a following peak to a following nadir to determine an instantaneous respiratory cycle length.

11. The heart monitor of claim 10, further comprising calculation of an inverse of instantaneous respiratory cycle length to determine an instantaneous respiratory rate.

12. The heart monitor of claim 10, wherein said trend of values comprises a respiratory component that is measured from a nadir to a following peak to determine inspiration time (TI) and wherein said trend of values comprises another respiratory component that is measured from a peak to a following nadir to determine expiration time (TE) and further comprising calculation of an instantaneous inspiration/expiration ratio or I/E ratio by dividing TI by TE.

13. The heart monitor of claim 1, wherein said trend of values comprises a respiratory component that is measured from a nadir to a following peak to determine an instantaneous tidal volume (TV).

14. The heart monitor of claim 1, wherein said trend of values comprises a respiratory component that is calculated by integration of an area under said trend of values for one minute to determine a minute ventilation.

15. The heart monitor of claim 1, wherein said trend of values is calculated to disregard under-threshold moves, and over-threshold moves in a direction opposite to a current up or down trend of values, such that if a current value of a point in time n is less than, or greater than, a current value at a previous point in time n−1, and less than, or greater than, a current value at a later in point in time n+1, then the value at point in time n is disregarded as neither a peak or a nadir.

16. A heart monitor configured to obtain respiration metrics comprising:
 an impedance signal input;
 an impedance measurement unit coupled with said impedance signal input;
 a microprocessor configured to obtain a first time series of values that represent a transthoracic impedance signal obtained from said impedance measurement unit;
 said microprocessor further configured to generate a modified time series of values that represent a trend of values of said first time series through application of at least one morphological operator wherein said trend of values comprises a respiratory component of said first times series;
 wherein said at least one morphological operator includes an erosion operator defined by $$F \ominus K(i) = \min_{j=0, \ldots, M-1} f_{i+j} - k_j$$

for $i = 0, 1, \ldots, N - M$ and also includes a dilation operator defined by $$F \odot K(i) = \max_{j=i-M+1, \ldots, i} f_j + k_{i-j}$$

for $i = M - 1, M, \ldots, N - 1$ where $F=[f_0, f_1, \ldots, f_{N-1}]$ is a discrete input signal comprising said first time series, and
where $K=[k_0, k_1, \ldots, k_{M-1}]$ is a predefined discrete kernel function, or structure element or SE, and where N and M are two integers that N>M and wherein K is a vector comprising all zeroes.

17. The heart monitor of claim 16, wherein said trend of values is calculated to disregard under-threshold moves, and over-threshold moves in a direction opposite to a current up or down trend of values, such that if a current value of a point in time n is less than, or greater than, a current value at a previous point in time n−1, and less than, or greater than, a current value at a later in point in time n+1, then the value at point in time n is disregarded as neither a peak or a nadir.

18. A heart monitor configured to obtain respiration metrics comprising:
 an impedance signal input;
 an impedance measurement unit coupled with said impedance signal input;
 a microprocessor configured to obtain a first time series of values that represent a transthoracic impedance signal obtained from said impedance measurement unit; and,
 said microprocessor further configured to
  generate a modified time series of values that represent a trend of values of said first time series through application of at least one morphological operator comprising
   an erosion operator or
   a dilation operator or
   any combination thereof
  wherein said trend of values comprises a respiratory component of said first times series;
  wherein said trend of values comprises a respiratory component that is measured from a nadir to a following peak to determine inspiration time (TI), and from a peak to following nadir to determine expiration time (TE);
  wherein said trend of values is calculated to disregard under-threshold moves, and over-threshold moves in a direction opposite to a current up or down trend of values, such that if a current value of a point in time n is less than, or greater than, a current value at a previous point in time n−1, and less than, or greater than, a current value at a later in point in time n+1, then the value at point in time n is disregarded as neither a peak or a nadir.

* * * * *